United States Patent [19]

Kashimura et al.

[11] Patent Number: 5,071,995

[45] Date of Patent: Dec. 10, 1991

[54] 2-HYDROXYPHENYLBENZOTRIAZOL COMPOUNDS AND THE USE THEREOF

[75] Inventors: Tsugunori Kashimura; Tsutomu Miura; Keiji Matsumura, all of Kurashiki, Japan

[73] Assignee: Kuraray Co., Ltd., Okayama, Japan

[21] Appl. No.: 414,399

[22] Filed: Sep. 29, 1989

[30] Foreign Application Priority Data

Oct. 7, 1988 [JP] Japan .................. 63-254656

[51] Int. Cl.$^5$ ............................. C07D 249/20
[52] U.S. Cl. ................... 548/260; 548/259; 548/261; 430/78
[58] Field of Search ............ 548/261, 259, 260

[56]  References Cited

U.S. PATENT DOCUMENTS

| | | | |
|---|---|---|---|
| 3,214,436 | 10/1955 | Boyle et al. | 548/260 |
| 3,272,891 | 9/1966 | Milionis et al. | 548/259 |
| 3,493,539 | 2/1970 | Skoultchi et al. | 548/259 |
| 3,936,418 | 2/1976 | Pond et al. | 548/259 |
| 4,863,802 | 9/1989 | Moore et al. | 548/261 |
| 4,891,396 | 1/1990 | Avar et al. | 548/259 |

FOREIGN PATENT DOCUMENTS 2413005 10/1975 Fed. Rep. of Germany ...... 548/261
57-35221 7/1982 Japan .

OTHER PUBLICATIONS

Chemical Abstracts, vol. 80, No. 10, 11 Mar. 1974, p. 57, Abstract No. 49159z; & JP-A-73-73450 (Asahi Chem. Ind.), 3 Oct. 1973.
Abstract No. 49159z; & JP-A-73-73450 (Asahi Chem. Ind.), 3 Oct. 1973.
Herlinger, Chem. Abstr., vol. 84, Entry 31086w, (1975).
Hill, Chem. Abstr., vol. 102, Entry 19616b, (1984).

*Primary Examiner*—Donald G. Daus
*Attorney, Agent, or Firm*—Oblon, Spivak, McClelland, Maier & Neustadt

[57]  ABSTRACT

Provided are 2-hydroxyphenylbenzotriazol compounds with excellent ultraviolet absorbability and high thermal stability. They can be used as ultraviolet absorber for any polymer.

1 Claim, No Drawings

2-HYDROXYPHENYLBENZOTRIAZOL COMPOUNDS AND THE USE THEREOF

BACKGROUND OF THE INVENTION

1. Field of the Invention

This invention relates to 2-hydroxybenzotriazol compounds and also to the use thereof.

2. Description of Prior Art

It is known that many polymers are degraded by the action of ultraviolet light. Polyolefins, polyesters, polyamides and the like are examples of polymers which deteriorate when exposed for a long time to ultraviolet light, e.g. sunlight.

Recently a variety of goods including foods such as refreshing drinks, alcoholic drinks edible oils, cosmetics, and medicines have been sold and stored in transparent plastic containers. Since ultraviolet light with a wavelength of about 250 to about 390 nm passes freely through such transparent plastic containers, the contents are subject to deterioration, discoloration and decomposition.

It is known that cyanoacrylate ultraviolet absorbers can be incorporated in the above-mentioned polymers for the purpose of protecting the polymers and the contents of the plastic containers from deterioration from ultraviolet light (cf. U.S. Pat. No. 4,617,374). It is also known that the incorporation by mixing or by copolymerization of benzotriazol ultraviolet absorbers in polymers can give ultraviolet absorptive capacity to the polymers (cf. Japanese Patent Publication No. 35221/1982 and U.S. Pat. No. 3,214,436).

However, cyanoacrylate ultraviolet absorbers are inferior to benzotriazol ultraviolet absorbers both in thermal stability and ultraviolet absorption. Further, the polymers obtainable by copolymerization of the benzotriazol ultraviolet absorbers described in the above-mentioned Japanese Patent Publication No. 35221/1982 have poor thermal resistance and have unsatisfactory ultraviolet absorbability. Polymers obtainable by copolymerization of the benzotriazol compound described in U.S. Pat. No. 3,214,436 have unsatisfactory ultraviolet absorbability.

Accordingly, an object of the present invention is to provide a novel 2-hydroxyphenylbenzotriazol compound having excellent ultraviolet absorptive capacity.

Another object of the invention is to provide the use of the novel 2-hydroxyphenylbenzotriazol compound as an ultraviolet absorber.

Still another object of the invention is to provide a polymer having excellent ultraviolet absorbability obtainable by incorporation of the novel 2-hydroxyphenylbenzotriazol compound.

Yet another object of the invention is to provide a polymer having excellent ultraviolet absorbability obtainable by copolymerization of the novel 2-hydroxyphenylbenzotriazol compound.

These objects as well as other objects and advantages of the present invention will become apparent to those skilled in the art from the following detailed description.

SUMMARY OF THE INVENTION

According to the present invention, there is provided a 2-hydroxyphenylbenzotriazol compound represented by the general formula (I)

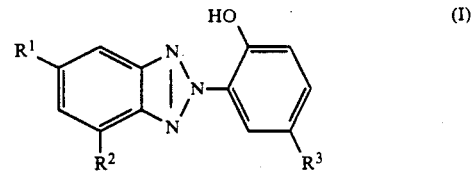

wherein $R^1$ and $R^3$ are each a carboxyl group, a halogen atom, a lower alkyl group or a lower alkoxyl group; $R^2$ is a carboxyl group, a hydrogen atom, a halogen atom, a lower alkyl group or a lower alkoxyl group; and two of $R^1$, $R^2$ and $R^3$ are carboxyl groups.

The present invention also provides an ultraviolet absorber comprising as an effective component the 2-hydroxyphenylbenzotriazol compound represented by the above general formula (I).

The present invention also provides a polymer containing in an amount of 0.001 to 5% by weight of the 2-hydroxyphenylbenzotriazol compound represented by the above general formula (I).

The present invention also provides a polymer containing as a copolymerized component in an amount of 0.001 to 5% by weight of the 2-hydroxyphenylbenzotriazol compound represented by the above general formula (I).

DESCRIPTION OF THE PREFERRED EMBODIMENTS

In the above general formula (I), examples of the halogen atoms represented by each of $R^1$, $R^2$ and $R^3$ are chlorine atom, bromine atom and the like; examples of the lower alkyl group are methyl, ethyl, n-propyl, i-propyl, n-butyl, i-butyl, sec-butyl, tert-butyl and the like; and examples of the lower alkoxyl group are methoxy, ethoxy, n-propoxy, i-propoxy, n-butoxy, i-butoxy, sec-butoxy, tert-butoxy and the like.

In the above general formula (I), it is necessary that two members selected from the group consisting of $R^1$, $R^2$ and $R^3$ be carboxyl groups. Polymers obtained by copolymerization of a 2-hydroxyphenylbenzotriazol compound having only one carboxyl group have a lower polymerization degree than polymers which do not contain 2-hydroxyphenylbenzotriazol compound as a copolymerization component. Polymers obtained by copolymerization of a 2-hydroxyphenylbenzotriazol compound having three carboxyl groups tend to crosslink and gel.

Typical examples of the 2-hydroxyphenylbenzotriazol compound represented by general formula (I) are:

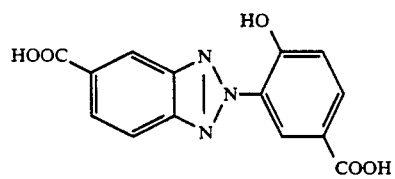

2-(2'-hydroxyphenyl)benzotriazol-5,5'-dicarboxylic acid

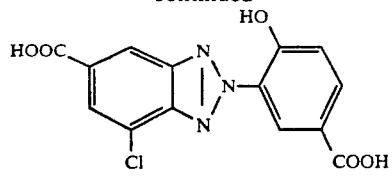

4-chloro-2-(2'-hydroxyphenyl)-benzo-
triazol-6,5'-dicarboxylic acid

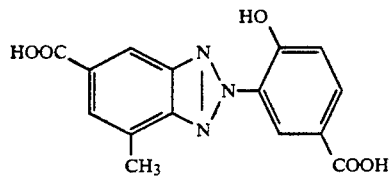

2-(2'-hydroxyphenyl)-4-methylbenzo-
triazol-6,5'-dicarboxylic acid

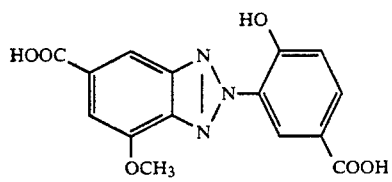

2-(2'-hydroxyphenyl)-4-methoxybenzo-
triazol-6,5'-dicarboxylic acid

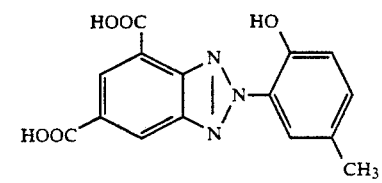

2-(2'-hydroxy-5'-methylphenyl)benzo-
triazol-4,6-dicarboxylic acid

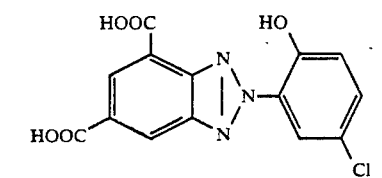

2-(5'-chloro-2'-hydroxyphenyl)benzo-
triazol-4,6-dicarboxylic acid

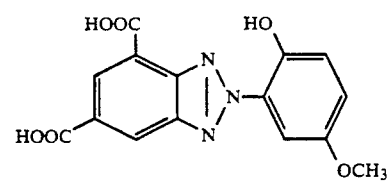

2-(2'-hydroxy-5'-methoxyphenyl)-
benzotriazol-4,6-dicarboxylic acid

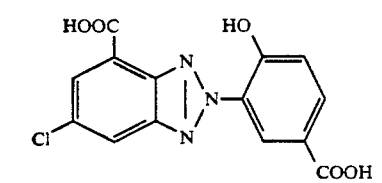

6-chloro-2-(2'-hydroxyphenyl)benzo-
triazol-4,5'-dicarboxylic acid

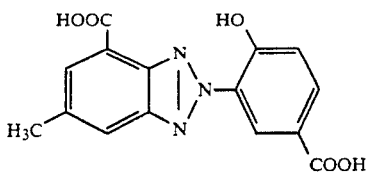

2-(2'-hydroxyphenyl)-6-methylbenzo-
triazol-4,5'-dicarboxylic acid

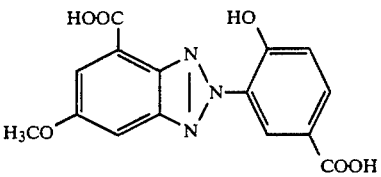

2-(2'-hydroxyphenyl)-6-methoxybenzo-
triazol-4,5'-dicarboxylic acid

The 2-hydroxyphenylbenzotriazol compound represented by general formula (I) can for example be produced by the following processes:

(Synthesis Process 1)

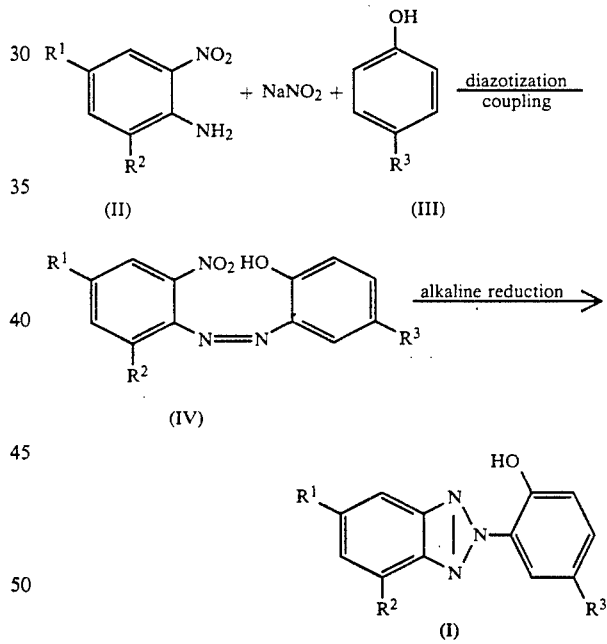

wherein $R^1$, $R^2$ and $R^3$ are as defined before.

In the above process, a nitroaniline compound represented by general formula (II) is diazotized in the usual way, and the obtained product is coupled to a phenol compound represented by general formula (III) in for example 10% aqueous sodium hydroxide solution at a temperature of 0° to 5° C. to give a nitroazo compound represented by general formula (IV). The thus obtained nitrozao compound is subjected to alkaline reduction using a metal such as zinc or tin, zinc chloride or the like reducing agent in for example an aqueous sodium hydroxide solution at a temperature of 40° C. or below to give a 2-hydroxyphenylbenzotriazol compound represented by formula (I). The phenol compound represented by general formula (III) is used in nearly equimolar amount to the nitroaniline compound represented by general formula (II). The above-mentioned reducing agents are used in about 3 to 10 molar equivalents of the nitroazo compound represented by general formula (IV).

(Synthesis Process 2)

Firstly, a 2-hydroxyphenylbenzotriazol compound having none or just one carboxyl group and 1 to 3 halogen atoms is synthesized according to Synthesis Process 1; or a 2-hydroxyphenylbenzotriazol compound having none or just one carboxyl group is reacted with 1.0 to 2.5 molar excess of a halogenation agent such as chlorine, bromine, hypochlorite or hypobromite to give a 2-hydroxyphenylbenzotriazol compound having 1 to 3 halogen atoms. The resulting 2-hydroxyphenylbenzotriazol compound having 1 to 3 halogen atoms is subjected to any one of the following reactions, to convert the halogen atoms to carboxyl groups, thus completing the preparation of the 2-hydroxyphenylbenzotriazol compound represented by general formula (I). Reactions employed herein are reaction with carbon monoxide in the presence of 0.05 to 1 mol % of an organometal catalyst containing, for example, nickel, iron, cobalt, palladium, rhodium, etc., reaction with carbon dioxide in the presence of 150 to 300 mol % of n-butyllithium or a Grinard reaction.

The 2-hydroxyphenylbenzotriazol compound represented by general formula (I) has an excellent ultraviolet absorbability and a high thermal stability and hence is useful as an ultraviolet absorber. The 2-hydroxyphenylbenzotriazol compound can be used as ultraviolet absorber for any polymer but, it is preferably used for condensation polymers such as polyesters and polyamides.

Examples of the above-mentioned polyesters are ones derived from dicarboxylic acid and diol such as those from aromatic dicarboxylic acid and aromatic diol, from aromatic dicarboxylic acid and aliphatic diol, from aliphatic dicarboxylic acid and aromatic diol and from aliphatic dicarboxylic acid and aliphatic diol; ones derived from oxycarboxylic acid and ones obtained by ring opening polymerization of lactone. Particularly preferred are polyesters comprising at least 50 mol % of an aromatic dicarboxylic acid in the dicarboxylic acid component and at least 80 mol % of the diol component of aliphatic or alicyclic diol having 2 to 10 carbon atoms. Examples of the aromatic dicarboxylic acid are terephthalic acid, isophthalic acid, 2,6-naphthalenedicarboxylic acid, and the like; and examples of the aliphatic dicarboxylic acid are adipic acid, azelaic acid, sebacic acid and the like. Examples of the aliphatic or alicyclic diol are ethylene glycol, propylene glycol, tetramethylene glycol, hexamethylene glycol, nonamethylene glycol, cyclohexanedimethanol, diethylene glycol and the like; and they are used singly or in combination of 2 or more. The polyesters may contain as a coporimerization component a tri- or more multifunctional compound such as glycerine, trimethylol propane, pentaerythritol, trimellitic acid, trimesic acid or pyromellitic acid within a limit which allows the obtained polyester to undergo melt formation. The polyesters are produced by conventional process generally employed for the preparation of polyesters, e.g. transesterification of a lower alkyl ester of a dicarboxylic acid with a diol followed by polycondensation, prepolymerization of a dicarboxylic acid and diol followed by polycondensation, and the like. The thus obtained polyesters preferably have an intrinsic viscosity measured in a 1:1 by weight mixture of phenol/tetrachloroethane at 30° C. of 0.3 to 1.5, more preferably 0.4 to 1.2.

Examples of the afore-mentioned polyamides are ones derived from dicarboxylic acid and diamine such as aromatic dicarboxylic acid and aromatic diamine, aromatic dicarboxylic acid and aliphatic diamine, aliphatic dicarboxylic acid and aromatic diamine, and aliphatic dicarboxylic acid and aliphatic diamine; and ones obtained by ring opening polymerization of lactam. Paricularly preferred are ones derived from aromatic dicarboxylic acid and aliphatic diamine, and from aliphatic dicarboxylic acid and aromatic diamine. Examples of the aromatic dicarboxylic acid are terephthalic acid, isophthalic acid, 2,6-naphthalenedicarboxylic acid and the like; and examples of the aliphatic dicarboxylic acid are adipic acid, azelaic acid, sebacic acid, and the like. Examples of the aromatic diamine are phenylenediamine, xylylenediamine, and the like; and examples of aliphatic diamine are tetramethylenediamine, hexamethylenediamine, octamethylenediamine, and the like; and they are used singly or in combination of two or more. The polyamides may contain a tri- or more multifunctional compound such as triaminobenzene, trimellitic acid, trimesic acid and pyromellitic acid as a copolymerization component within a limit which allows the obtained polyamide to undergo melt formation. The polyamides are produced by conventional processes for the preparation of polyamides, such as preparation of nylon salt from a dicarboxylic acid and a diamine followed by polycondensation, interfacial polymerization of a dicarboxylic acid halide and a diamine, and the like. The thus obtained polyamides preferably have a relative viscosity measured in 98% concentrated sulfuric acid at 25° C. of 1.4 to 3.5, more preferably 1.8 to 3.0.

The ultraviolet absorbers provided by the present invention are incorporated into a polymer in an amount of 0.001 to 10 wt % based on the weight of the polymer. The incorporation amount is preferably within the range of from 0.01 to 5 wt %, and more preferably within the range of from 0.05 to 2 wt %. Polymers incorporating the ultraviolet absorber in an amount less than 0.001 wt % has low absorbability for ultraviolet light, while polymers with the ultraviolet absorber in an amount exceeding 10 wt % may sometimes be of inferior physical properties.

The ultraviolet absorber of the present invention can be incorporated in a polymer at any stage of polymer production and it can also be incorporated before or during molding process of the polymer in the usual way. Then, the ultraviolet absorber is present in a polymer either mixed or copolymerized therewith.

The ultraviolet absorber of the present invention can also be used together with, as required, other additives such as a colorant, antistatic agent, flame retardent, filler and plasticizer.

It is preferred that polymers having incorporated the ultraviolet absorbers of the present invention be ones having copolymerized the 2-hydroxyphenylbenzotriazol compound represented by general formula (I) in such a way that its end binds the main chain or the branch of the polymer by ester-bond or amide-bond.

In the case where polymers having incorporated the 2-hydroxyphenylbenzotriazol compound represented by general formula (I) is diluted with another polymer compatible therewith, the dilution should be conducted such that the incorporation amount of the 2-hydroxyphenylbenzotriazol compound represented by general formula (I) falls within the afore-specified range after the dilution.

The polymers provided by the present invention have excellent ultraviolet absorbability. Among such polymers, those containing the 2-hydroxyphenylbenzotriazol compound represented by general formula (I) as a copolymerization component is preferred since the ultraviolet absorbing component cannot be extracted from such a polymer. The polymers of the present invention can be melt molded by known processes such as injection molding, blow molding, biaxial-drawing molding, vacuum molding and compression molding. Furthermore, the polymers of the present invention can also be used while being blended or laminated with other polymers.

Packaging materials, containers and the like obtainable by molding the polymer of the present invention have excellent ultraviolet absorbability, thus capable of shutting off the passage of ultraviolet light to thereby effectively protect the contents from deterioration or degradation.

EXAMPLES

Other features of the invention will become apparent in the course of the following descriptions of exemplary embodiments which are given for illustration of the invention and are not intended to be limiting thereof. In the Examples, "parts" means "parts by weight", and various properties were measured according to methods described below.

(1) Ultraviolet spectrum

A spectrophotometer, UV-2100, available from Shimazu Corporation was used. A solution of 10 mg/l specimen 2-hydroxyphenylbenzotriazol compound in ethanol was tested, and a solution of specimen polymer solution in 1:1 by weight mixture of phenol/tetrachloroethane was tested.

(2) Extractability

A solution was prepared by dissolving 1 g of specimen polymer in 200 ml of 1:1 by weight mixture of phenol/tetrachloroethane. The solution was added to about 2 liters of methanol, and the polymer precipitated was separated by filtration. Ultraviolet spectra of the polymer before and after this extraction procedure were compared.

(3) Intrinsic viscosity, [$\eta$]

Measured on a 10 g/l solution in 1:1 by weight mixture of phenol/tetrachloroethane at 30° C.

(4) Relative viscosity, $\eta_{rel}$

Measured according to JIS K6810 (ASTM D789-86) on a 10 g/l solution in 98% concentrated sulfuric acid at 25° C.

(5) Melting point, Tm, and glass transition temperature, Tg

Specimen of quenched amorphous state was tested with a DSC, type TA-3000 available from Mettler, at a temperature elevating rate of 10° C./min.

EXAMPLE 1

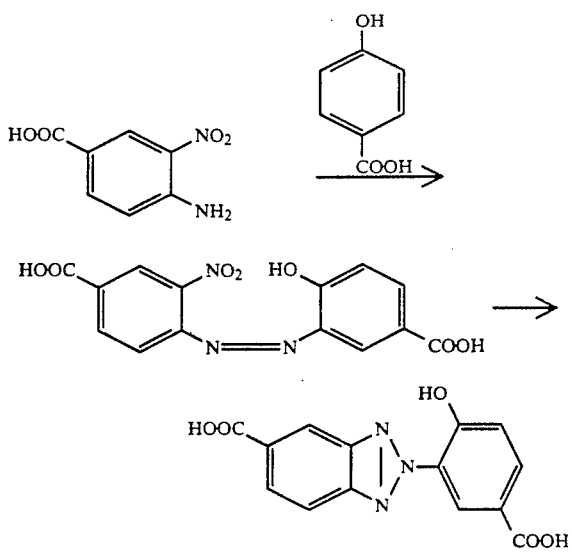

A diazonium salt solution was prepared by diazotization of 36.4 g (200 mmoles) of 4-amino-3-nitrobenzoic acid with 60 g (600 mmoles) of concentrated hydrochloric acid and 13.8 g (200 mmoles) of sodium nitrite in the usual way. The diazonium salt solution obtained was gradually added to 200 ml of 10 wt % aqueous sodium hydroxide solution containing 27.6 g (200 mmoles) of p-hydroxybenzoic acid kept within the temperature range of from 0° to 5° C. The mixture was stirred for 2 hours and a nitroazo compound precipitated was separated by filtration. The yield was 64%.

The nitroazo compound (28.7 g, 100 mmoles) obtained was dissolved in 100 ml of 2N aqueous sodium hydroxide solution, and the obtained solution was gradually added to 50 ml of 25% aqueous sodium hydroxide solution containing zinc dust (30 g, 460 mmoles) kept at a temperature not higher than 40° C. The reaction mixture was cooled to a temperature below 30° C., acidified (pH=1 to 2) with concentrated hydrochloric acid and then stirred for 2 hours. The reaction reaction mixture was alkalized (pH=13 to 14) with sodium hydroxide, and filtered through a glass filter. The filtrate was again acidified (pH=1 to 2) and precipitate was collected by filtration. The precipitate was washed with cool water, dried, and then recrystallized from water-methanol solution to give 16.1 g of a light brown crystal of 2-(2'-hydroxyphenyl)benzotriazol-5,5'-dicarboxylic acid. The yield was 54%.

The wavelength of the maximal absorption of ultraviolet light on the product obtained, in ethanol, was 334 nm. The analysis results of the product are as follows.

| | Elemental analysis | |
|---|---|---|
| | Calcd. (as $C_{14}H_9N_3O_5$) | Found |
| C % | 56.19 | 55.95 |
| H % | 3.03 | 3.00 |
| N % | 14.04 | 13.89 |

Mass spectrometery 299 (M+)

EXAMPLE 2

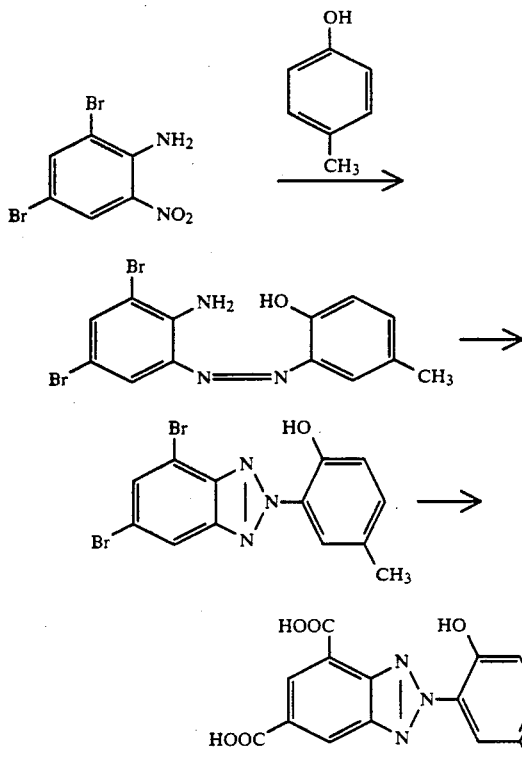

In glacial acetic acid, 55.2 g (400 mmoles) of o-nitroaniline was reacted with 150.2 g (940 mmoles) of bromine to give 85.2 g (288 mmoles) of 2,4-dibromo-6-nitroaniline.

Example 1 was repeated except that 59.2 g (200 mmoles) of the 2,4-dibromo-6-nitroaniline and 21.6 g (200 mmoles) of p-methylphenol were used instead of 36.4 g (200 mmoles) of 4-amino-3-nitrobenzoic acid and 27.6 g (200 mmoles) of p-hydroxybenzoic acid respectively to obtain 4,6-dibromo-2-(2'-hydroxy-5'-methylphenyl)benzotriazol. The yield was 60%.

In petroleum ether, 14.1 g (220 mmoles) of lithium-n-butyl was added to 38.3 g (100 mmoles) of the 4,6-dibromo-2-(2'-hydroxy-5'-methylphenyl)benzotriazol thus obtained. The mixture was refluxed for 24 hours and then reacted with dry ice to give 22.2 g of 2-(2'-hydroxy-5'-methylphenyl)benzotriazol-4,6-dicarboxylic acid. The yield was 71%.

The wavelength of the maximal absorption of ultraviolet light on the product obtained, in ethanol, was 334 nm. The analysis results of the product are as follows.

| | Elemental analysis | |
|---|---|---|
| | Calcd. (as $C_{15}H_{11}N_3O_5$) | Found |
| C % | 57.51 | 57.18 |
| H % | 3.54 | 3.43 |
| N % | 13.41 | 13.03 |

Mass spectrometery 313 ($M^+$)

EXAMPLE 3

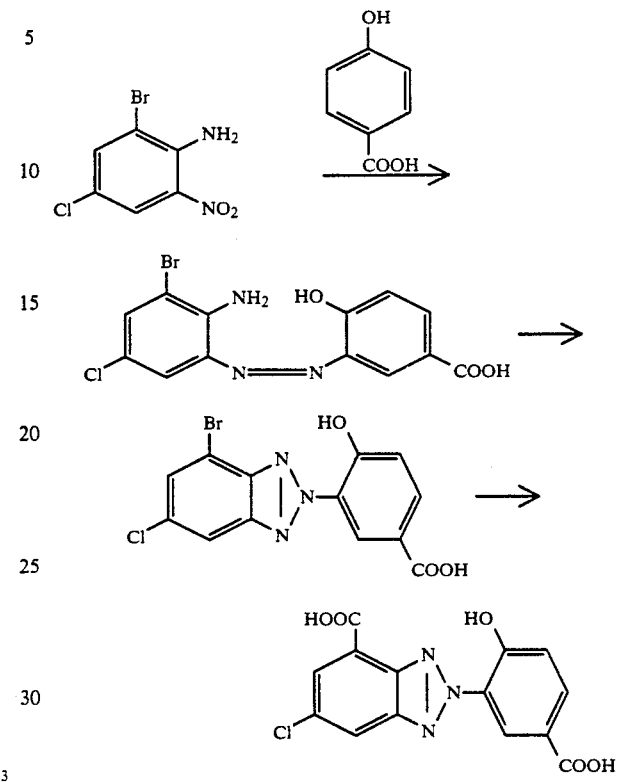

In glacial acetic acid, 51.8 g (300 mmoles) of 4-chloro-2-nitroaniline was reacted with 57.5 g (360 mmoles) of bromine to give 61.6 g (243 mmoles) of 6-bromo-4-chloro-2-nitroaniline.

Example 1 was repeated except that 50.3 g (200 mmoles) of the 6-bromo-4-chloro-2-nitroaniline was used instead of 36.4 g (200 mmoles) of 4-amino-3-nitrobenzoic acid to obtain 4-bromo-6-chloro-2-(2'-hydroxyphenyl)-benzotriazol-5'-carboxylic acid. The yield was 58%.

In petroleum ether 9.6 g (150 mmoles) of n-butyl lithium was added to 36.8 g (100 mmoles) of the 4-bromo-6-chloro-2-(2'-hydroxyphenyl)-benzotriazol-5'-carboxylic acid thus obtained. The mixture was refluxed for 10 minutes and then reacted with dry ice to give 22.8 g of 6-chloro-2-(2'-hydroxyphenyl)benzotriazol-4,5'-dicarboxylic acid. The yield was 45%.

The wavelength of the maximal absorption of ultraviolet light on the product obtained, in ethanol, was 333 nm. The analysis results of the product are as follows.

| | Elemental analysis | |
|---|---|---|
| | Calcd. (as $C_{14}H_8N_3O_5Cl$) | Found |
| C % | 50.39 | 50.10 |
| H % | 2.42 | 2.38 |
| N % | 12.59 | 12.77 |
| Cl % | 10.62 | 10.91 |

Mass spectrometery 334 ($M^+$)

COMPARATIVE EXAMPLE 1

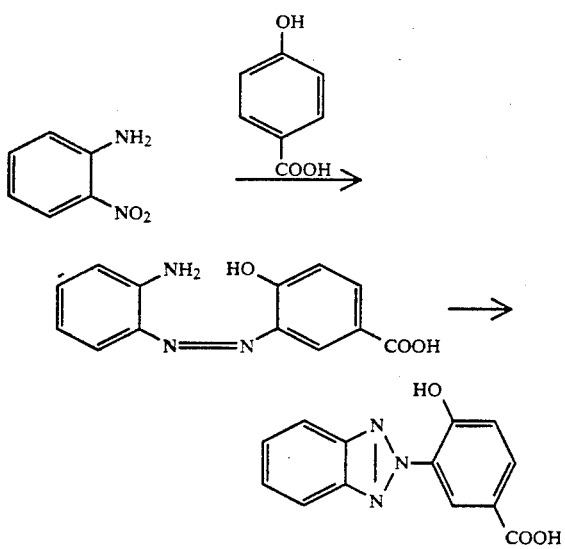

Example 1 was repeated except that 27.6 g (200 mmoles) of o-nitroaniline was used instead of 36.4 g (200 mmoles) of 4-amino-3-nitrobenzoic acid to obtain 13.3 g of 2-(2'-hydroxyphenyl)benzotriazol-5'-carboxylic acid. The yield was 52%.

The wavelength of the maximal absorption of ultraviolet light on the product obtained, in ethanol, was 332 nm. The analysis results of the product are as follows.

| Elemental analysis | | |
|---|---|---|
| | Calcd. (as $C_{13}H_9N_3O_5$) | Found |
| C % | 61.17 | 60.92 |
| H % | 3.55 | 3.52 |
| N % | 16.46 | 16.25 |

Mass spectrometery 255 (M+)

COMPARATIVE EXAMPLE 2

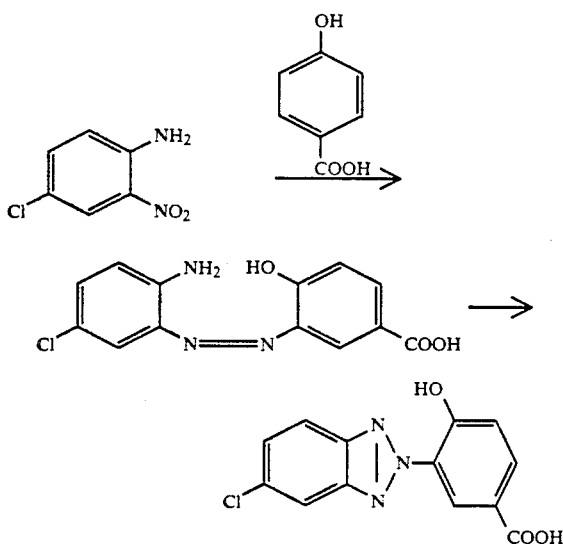

Example 1 was repeated except that 34.5 g (200 mmoles) of 4-chloro-2-nitroaniline was used instead of 36.4 g (200 mmoles) of 4-amino-3-nitrobenzoic acid to obtain 17.4 g of 5-chloro-2-(2'-hydroxyphenyl)benzotriazol-5'-carboxylic acid. The yield was 30%.

The wavelength of the maximal absorption of ultraviolet light on the product obtained, in ethanol, was 332 nm. The analysis results of the product are as follows.

| Elemental analysis | | |
|---|---|---|
| | Calcd. (as $C_{13}H_8N_3O_3Cl$) | Found |
| C % | 53.90 | 53.75 |
| H % | 2.78 | 2.60 |
| N % | 14.51 | 14.22 |
| Cl % | 12.24 | 12.23 |

Mass spectrometery 290 (M+)

COMPARATIVE EXAMPLE 3

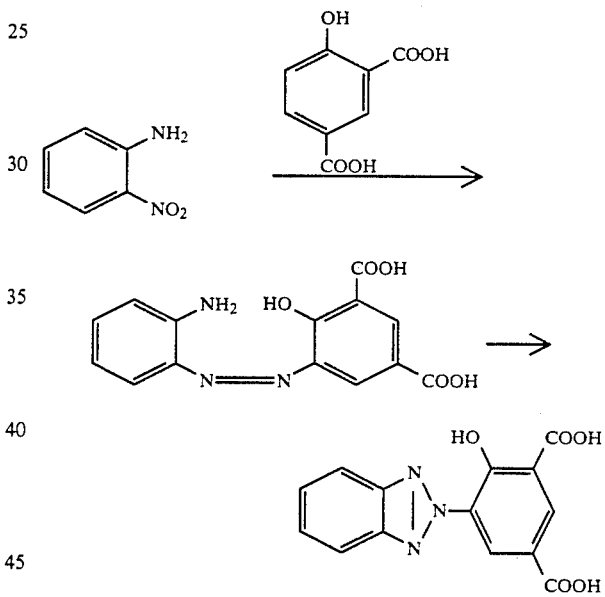

Comparative Example 1 was repeated except that 36.4 g (200 mmoles) of 4-hydroxyisophthalic acid was used instead of 27.6 g (200 mmoles) of p-hydroxybenzoic acid to obtain 26.9 g of 2-(2'-hydroxyphenyl)benzotriazol-3',5'-dicarboxylic acid. The yield was 45%.

The wavelength of the maximal absorption of ultraviolet light on the product obtained, in ethanol, was 310 nm. The analysis results of the product are as follows.

| Elemental analysis | | |
|---|---|---|
| | Calcd. (as $C_{14}H_9N_3O_5$) | Found |
| C % | 56.19 | 56.28 |
| H % | 3.03 | 3.29 |
| N % | 14.04 | 14.08 |

Mass spectrometery 299 (M+)

COMPARATIVE EXAMPLE 4

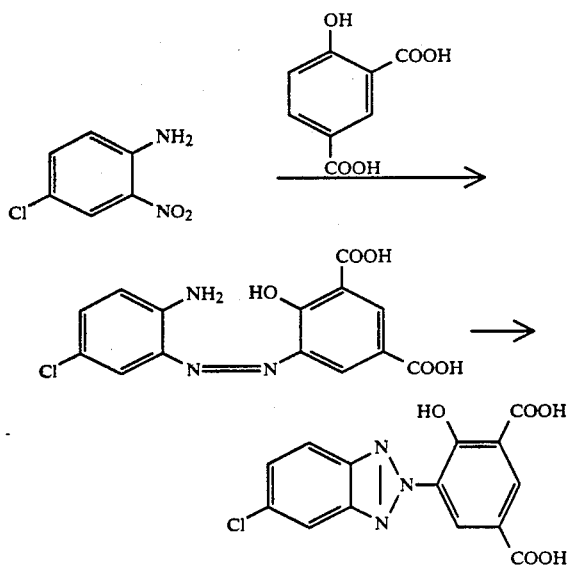

Comparative Example 3 was repeated except that 34.5 g (200 mmoles) of 4-chloro-2-nitroaniline was used instead of 27.6 g (200 mmoles) of o-nitroaniline to obtain 30.7 g of 5-chloro-2-(2'-hydroxyphenyl)benzotriazol-3',5'-dicarboxylic acid. The yield was 46%.

The wavelength of the maximal absorption of ultraviolet light on the product obtained, in ethanol, was 320 nm. The analysis results of the product are as follows.

| | Elemental analysis | |
| --- | --- | --- |
| | Calcd. (as $C_{14}H_8N_3O_5Cl$) | Found |
| C % | 50.39 | 50.02 |
| H % | 2.42 | 2.48 |
| N % | 12.59 | 12.90 |
| Cl % | 10.62 | 10.55 |

Mass spectrometery 334 (M+)

The 2-hydroxyphenylbenzotriazol compounds represented by general formula (I) and obtained in Examples 1 through 3 and Comparative Examples 1 through 4 are shown in Table 1.

TABLE 1

| Example or Comparative Example | Structural formula | Isolated yield (%) | Wavelength at maximal absorption of ultraviolet light (nm) |
| --- | --- | --- | --- |
| Example 1 | | 54 | 334 |
| Example 2 | | 43 | 334 |
| Example 3 | | 45 | 333 |
| Comparative Example 1 | | 52 | 322 |
| Comparative Example 2 | | 30 | 332 |

TABLE 1-continued

| Example or Comparative Example | Structural formula | Isolated yield (%) | Wavelength at maximal absorption of ultraviolet light (nm) |
| --- | --- | --- | --- |
| Comparative Example 3 | benzotriazole-N2-linked to phenyl with HO, COOH (ortho), and COOH (para) | 45 | 310 |
| Comparative Example 4 | 5-chloro-benzotriazole-N2-linked to phenyl with HO, COOH (ortho), and COOH (para) | 46 | 320 |

EXAMPLE 4

A reaction vessel was charged at a room temperature with 1,000 parts of dimethyl terephthalate, 720 parts of ethylene glycol (molar ratio of ethylene glycol to dimethyl terephthalate is 2.25 to 1) and 0.3 part of manganese acetate tetrahydrate. The mixture was heated to 140° C. and then gradually heated to 240° C. over about 3 hours with stirring to distill off at least 99% of theoretical amount of methanol. To the reaction mixture were added 0.1 part of phosphorous acid, 0.5 part of germanium dioxide and 4.9 parts of the 2-(2'-hydroxyphenyl)-benzotriazol-5,5'-dicarboxylic acid obtained in Example 1, and the mixture was allowed to undergo polycondensation for about 2 hours at 280° C. under a pressure of not higher than 0.5 mmHg. The polyester obtained showed an intrinsic viscosity, [η], of 0.82, a melting point of 248.1° C. and a glass transition temperature of 80.2° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 5

Example 4 was repeated except for using 0.5 parts instead of 4.9 parts of 2-(2'-hydroxyphenyl)benzotriazol-5,5'-dicarboxylic acid to obtain a polyester. The polyester obtained showed an intrinsic viscosity, [η], of 0.83, a melting point of 250.1° C. and a glass transition temperature of 80.5° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 6

Example 4 was repeated except for using 9.8 parts instead of 4.9 parts of 2-(2'-hydroxyphenyl)benzotriazol-5,5'-dicarboxylic acid to obtain a polyester. The polyester obtained showed an intrinsic viscosity, [ηρ, of 0.74, a melting point of 246.2° C. and a glass transition temperature of 79.6° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 7

Example 4 was repeated except for using 49 parts instead of 4.9 parts of 2-(2'-hydroxyphenyl)benzotriazol-5,5'-dicarboxylic acid to obtain a polyester. The polyester obtained showed an intrinsic viscosity, [η], of 0.76, a melting point of 245.6° C. and a glass transition temperature of 79.3° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 8

Example 4 was repeated except for using 73.5 parts instead of 4.9 parts of 2-(2'-hydroxyphenyl)benzotriazol-5,5'-dicarboxylic acid to obtain a polyester. The polyester obtained showed an intrinsic viscosity, [η], of 0.74, a melting point of 242.1° C. and a glass transition temperature of 78.9° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 9

Example 4 was repeated except for using 4.9 parts of the 2-(2'-hydroxy-5'-methylphenyl)benzotriazol-4,6-dicarboxylic acid obtained in Example 2 instead of 4.9 parts of 2-(2'-hydroxyphenyl)benzotriazol-5,5'-dicarboxylic acid to obtain a polyester. The polyester obtained showed an intrinsic viscosity, [η], of 0.77, a melting point of 250.2° C. and a glass transition temperature of 79.9° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 10

Example 4 was repeated except for using 1,000 parts of dimethyl isophthalate instead of 1,000 parts of dimethyl terephthalate to obtain a polyester. The polyester obtained showed an intrinsic viscosity, $[\eta]$, of 0.78 and a glass transition temperature of 64.5° C.

The polyester was tested for extractability. Ultraviolet absorption spectra of specimens before and after extraction were compared, and then it was found that both were just the same. The ultraviolet absorption behavior of the specimen after extraction is shown in Table 2.

EXAMPLE 11

Example 4 was repeated except for using 4.9 parts of the 6-chloro-2-(2'-hydroxyphenyl)benzotriazol-4,5'-dicarboxylic acid obtained in Example 3 instead of 4.9 parts of 2-(2'-hydroxyphenyl)benzotriazol-5,5'-dicarboxylic acid to obtain a polyester. The polyester obtained showed an intrinsic viscosity, $[\eta]$, of 0.79, a melting point of 250.6° C. and a glass transition temperature of 80.0° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 5

Example 4 was repeated except that 2-(2'-hydroxyphenyl)benzotriazol-5,5'-dicarboxylic acid was not used, to obtain a polyester. The polyester obtained showed an intrinsic viscosity, $[\eta]$, of 0.75, a melting point of 252.9° C. and a glass transition temperature of 80.6° C. The ultraviolet absorption behavior of the polyester is shown in Table 2.

COMPARATIVE EXAMPLE 6

Comparative Example 5 was repeated except for using 1,000 parts of dimethyl isophthalate instead of 1,000 parts of dimethyl terephthalate to obtain a polyester. The polyester obtained showed an intrinsic viscosity, $[\eta]$, of 0.70 and a glass transition temperature of 65.0° C.

The ultraviolet absorption behavior of the polyester is shown in Table 2.

COMPARATIVE EXAMPLE 7

Example 4 was repeated except for using 4.9 parts of the 2-(2'-hydroxyphenyl)benzotriazol-5'-carboxylic acid obtained in Comparative Example 1 instead of 4.9 parts of 2-(2'-hydroxyphenyl)benzotriazol-5,5'-dicarboxylic acid to obtain a polyester. The polyester obtained showed an intrinsic viscosity, $[\eta]$, of 0.80, a melting point of 248.1° C. and a glass transition temperature of 79.7° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 8

Example 4 was repeated except for using 4.9 parts of the 5-chloro-2-(2'-hydroxyphenyl)benzotriazol-5'-carboxylic acid obtained in Comparative Example 2 instead of 4.9 parts of 2-(2'-hydroxyphenyl)benzotriazol-5,5'-dicarboxylic acid to obtain a polyester. The polyester obtained showed an intrinsic viscosity, $[\eta]$, of 0.74, a melting point of 249.4° C. and a glass transition temperature of 79.5° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 9

Example 4 was repeated except for using 4.9 parts of the 2-(2'-hydroxyphenyl)benzotriazol-3',5'-dicarboxylic acid obtained in Comparative Example 3 instead of 4.9 parts of 2-(2'-hydroxyphenyl)benzotriazol-5,5'-dicarboxylic acid to obtain a polyester. The polyester obtained showed an intrinsic viscosity, $[\eta]$, of 0.78, a melting point of 252.1° C. and a glass transition temperature of 80.0° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 10

Example 4 was repeated except for using 4.9 parts of the 5-chloro-2-(2'-hydroxyphenyl)benzotriazol-3',5'-dicarboxylic acid obtained in Comparative Example 4 instead of 4.9 parts of 2-(2'-hydroxyphenyl)benzotriazol-5,5'-dicarboxylic acid to obtain a polyester. The polyester obtained showed an intrinsic viscosity, $[\eta]$, of 0.76, a melting point of 249.7° C. and a glass transition temperature of 79.9° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 11

Example 7 was repeated except for using 49 parts of the 2-(2'-hydroxyphenyl)benzotriazol-5'-carboxylic acid obtained in Comparative Example 1 instead of 49 parts of 2-(2'-hydroxyphenyl)benzotriazol-5,5'-dicarboxylic acid to obtain a polyester. The polyester obtained showed an intrinsic viscosity, $[\eta]$, of 0.33, a melting point of 253.4° C. and a glass transition temperature of 71.2° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 12

Example 4 was repeated except for using 0.005 part instead of 4.9 parts of 2-(2'-hydroxyphenyl)benzotriazol-5,5'-dicarboxylic acid to obtain a polyester. The polyester obtained showed an intrinsic viscosity, [η], of 0.76, a melting point of 252.1° C. and a glass transition temperature of 80.4° C.

The polyester was tested for extractability. Ultraviolet absorption spectra of specimens before and after extraction were compared, and then it was found that both were just the same. The ultraviolet absorption behavior of the specimen after extraction is shown in Table 2.

COMPARATIVE EXAMPLE 13

Example 4 was repeated except for using 4.9 parts of an ultraviolet absorber represented by the following structural formula instead of 4.9 parts of 2-(2'-hydroxyphenyl)benzotriazol-5,5'-dicarboxylic acid to obtain a polyester. The polyester obtained showed an intrinsic viscosity, [η], of 0.78, a melting point of 252.7° C. and a glass transition temperature of 80.3° C.

The polyester was tested for extractability. Ultraviolet absorption spectra of specimens before and after extraction are shown in Table 2.

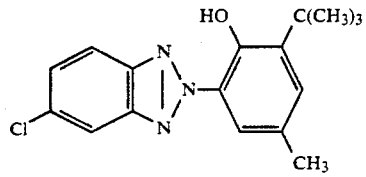

COMPARATIVE EXAMPLE 14

Example 4 was repeated except for using 4.9 parts of an ultraviolet absorber represented by the following structural formula instead of 4.9 parts of 2-(2'-hydroxyphenyl)benzotriazol-5,5'-dicarboxylic acid to obtain a polyester. The polyester obtained showed an intrinsic viscosity, [η], of 0.77, a melting point of 252.9° C. and a glass transition temperature of 80.0° C.

The polyester was tested for extractability. Ultraviolet absorption spectra of specimens before and after extraction are shown in Table 2.

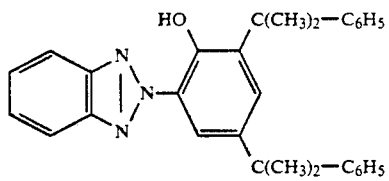

COMPARATIVE EXAMPLE 15

Example 4 was repeated except for using 4.9 parts of an ultraviolet absorber represented by the following structural formula instead of 4.9 parts of 2-(2'-hydroxyphenyl)benzotriazol-5,5'-dicarboxylic acid to obtain a polyester. The polyester obtained showed an intrinsic viscosity, [η], of 0.75, a melting point of 250.3° C. and a glass transition temperature of 79.7° C.

The polyester was tested for extractability. Ultraviolet absorption spectra of specimens before and after extraction were compared, and then it was found that both were just the same. The ultraviolet absorption behavior of the specimen after extraction is shown in Table 2.

As apparent from Table 2, the polyester has an extremely lower ultraviolet absorbability than those of Examples 4 through 11.

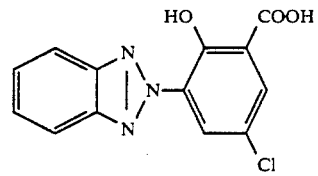

COMPARATIVE EXAMPLE 16

Example 7 was repeated except for using 20 parts of an ultraviolet absorber represented by the following structural formula instead of 49 parts of 2-(2'-hydroxyphenyl)benzotriazol-5,5'-dicarboxylic acid to obtain a polyester. The polyester obtained showed an intrinsic viscosity, [η], of 0.62, a melting point of 245.2° C. and a glass transition temperature of 70.8° C. Accordingly, the polyester had a remarkably lower thermal stability than those of the polyesters obtained in Examples 1 through 9 and Example 11.

The polyester was tested for extractability. Ultraviolet absorption spectra of specimens before and after extraction were compared, and then it was found that both were just the same. The ultraviolet absorption behavior of the specimen after extraction is shown in Table 2.

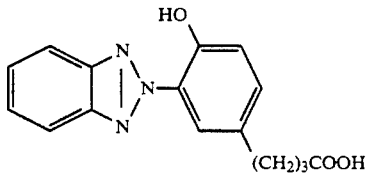

TABLE 2

|  | Intrinsic viscosity [η] | Melting point °C. | Glass transition temperature °C. | Light transmittance (%) | | | | | |
|---|---|---|---|---|---|---|---|---|---|
|  |  |  |  | 320 nm | 340 nm | 360 nm | 380 nm | 390 nm | 400 nm |
| Example 4 | 0.82 | 248.1 | 80.2 | 0 | 0 | 0.3 | 30.7 | 74.5 | 90.0 |
| Example 5 | 0.83 | 250.1 | 80.5 | 0 | 0 | 5.0 | 55.3 | 84.3 | 95.3 |
| Example 6 | 0.74 | 246.2 | 79.6 | 0 | 0 | 0 | 8.3 | 63.1 | 86.7 |
| Example 7 | 0.76 | 245.6 | 79.3 | 0 | 0 | 0 | 0 | 21.8 | 73.5 |
| Example 8 | 0.74 | 242.1 | 78.9 | 0 | 0 | 0 | 0 | 5.0 | 65.3 |
| Example 9 | 0.77 | 250.2 | 79.9 | 0 | 0 | 0.5 | 32.8 | 73.2 | 92.8 |
| Example 10 | 0.78 | — | 64.5 | 0 | 0 | 0.7 | 37.4 | 75.8 | 91.4 |
| Example 11 | 0.79 | 250.6 | 80.0 | 0 | 0 | 0.9 | 38.2 | 79.5 | 94.6 |
| Comparative Example 5 | 0.75 | 252.9 | 80.6 | 0 | 6.7 | 68.2 | 93.3 | 95.8 | 97.9 |
| Comparative | 0.70 | — | 65.0 | 17.2 | 87.4 | 96.0 | 97.1 | 97.6 | 98.1 |

TABLE 2-continued

| | Intrinsic viscosity [η] | Melting point °C. | Glass transition temperature °C. | | Light transmittance (%) | | | | | |
|---|---|---|---|---|---|---|---|---|---|---|
| | | | | | 320 nm | 340 nm | 360 nm | 380 nm | 390 nm | 400 nm |
| Example 6 Comparative Example 7 | 0.80 | 248.1 | 79.7 | | 0 | 0.7 | 7.3 | 84.7 | 91.7 | 93.3 |
| Comparative Example 8 | 0.74 | 249.4 | 79.5 | | 0 | 0.7 | 21.2 | 76.8 | 84.8 | 87.0 |
| Comparative Example 9 | 0.78 | 252.1 | 80.0 | | 0 | 1.0 | 49.7 | 86.0 | 91.9 | 94.0 |
| Comparative Example 10 | 0.76 | 249.7 | 79.9 | | 0 | 1.0 | 42.5 | 75.2 | 92.2 | 95.0 |
| Comparative Example 11 | 0.33 | 253.4 | 71.2 | | 0 | 0 | 0 | 7.8 | 43.4 | 78.2 |
| Comparative Example 12 | 0.76 | 252.1 | 80.4 | | 0 | 4.0 | 62.6 | 91.9 | 96.0 | 97.2 |
| Comparative Example 13 | 0.78 | 252.7 | 80.3 | before extraction | 0 | 5.9 | 67.6 | 89.9 | 92.9 | 96.0 |
| | | | | after extraction | 0 | 5.9 | 67.8 | 90.0 | 93.9 | 96.5 |
| Comparative Example 14 | 0.77 | 252.9 | 80.0 | before extraction | 0 | 2.0 | 22.2 | 57.6 | 75.8 | 89.5 |
| | | | | after extraction | 0 | 5.5 | 60.2 | 88.9 | 92.9 | 95.4 |
| Comparative Example 15 | 0.75 | 250.3 | 79.7 | | 0 | 0 | 23.4 | 81.2 | 93.7 | 95.6 |
| Comparative Example 16 | 0.62 | 245.2 | 70.8 | | 0 | 0 | 2.1 | 47.8 | 68.3 | 87.0 |

EXAMPLE 12

An autoclave was charged with 429 parts of terephthalic acid, 1,000 parts of isophthalic acid, 10.6 parts of the 2-(2'-hydroxyphenyl)benzotriazol-5,5'-dicarboxylic acid obtained in Example 1, 1,050 parts of hexamethylenediamine, 10.5 parts of benzoic acid, 614 parts of deionized water and 1.8 parts of sodium hypophosphite. After thorough replacement of internal atmosphere with nitrogen, the autoclave was heated while being kept airtight. The contents were stirred for about 1 hour with the internal pressure and internal temperature being controlled to be 9 to 10 kg/cm² and 190° to 200° C. respectively to effect reaction. The heating was resumed to an internal pressure of 18 kg/cm² and polymerization reaction was initiated with stirring while pressure is released to maintain the internal pressure. Heating was continued over 5 hours from 200° C. upto 250° C., and pressure is released when water no longer distilled off and then a polyamide was taken out. The polyamide thus obtained showed a relative viscosity, $\eta_{rel}$, of 2.26 and a glass transition temperature of 126.4° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 13

Example 12 was repeated except for using 2.1 parts instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.10 and a glass transition temperature of 127.0° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 14

Example 12 was repeated except for using 21.2 parts instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.10 and a glass transition temperature of 127.0° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 15

Example 12 was repeated except for using 106 parts instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.08 and a glass transition temperature of 126.6° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 16

Example 12 was repeated except for using 10.6 parts of the 2-(2'-hydroxy-5'-methylphenyl)benzotriazol-4,6-dicarboxylic acid obtained in Example 2 instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.08 and a glass transition temperature of 126.6° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 17

An autoclave was charged with 1,000 parts of adipic acid, 8.4 parts of the 2-(2'-hydroxyphenyl)benzotriazol-5,5'-dicarboxylic acid obtained in Example 1, 955 parts of m-xylylenediamine, 7.0 parts of benzoic acid, 409 parts of deionized water and 1.2 parts of sodium hypophosphite. After thorough replacement of internal atmosphere with nitrogen, the autoclave was heated with stirring for 1 hour while being kept airtight, with the internal pressure and internal temperature being controlled to be 9 to 10 kg/cm$^2$ and 190° to 200° C. respectively, to effect reaction. The heating was resumed to an internal pressure of 18 kg/cm$^2$ and polymerization reaction was initiated with stirring while pressure is released to maintain the internal pressure. Heating was continued over 5 hours from 200° C. upto 270° C., and pressure is released when water no longer distilled off and then a polyamide was taken out. The polyamide thus obtained showed a relative viscosity, $\eta_{rel}$, of 2.19, a glass transition temperature of 86.1° C. and a melting point of 230.2° C.

The polyamide was tested for extractability. Ultraviolet absorption spectra of specimens before and after extraction were compared, and then it was found that both were just the same. The ultraviolet absorption behavior of the specimen after extraction is shown in Table 3.

EXAMPLE 18

There were prepared 25 wt % methanol solutions by dissolving 1,000 parts of hexamethylenediamine, 1,254 parts of adipic acid and 8.3 parts of the 2-(2'-hydroxyphenyl)benzotriazol-5,5'-dicarboxylic acid obtained in Example 1 in methanol respectively. The solutions were gradually mixed with each other to give a nylon salt. The nylon salt obtained and the same weight of water were charged to an autoclave. After thorough replacement of internal atmosphere with nitrogen, the autoclave was heated with stirring for 4 hour while being kept airtight, with the internal pressure and internal temperature being controlled to be 10 to 17.5 kg/cm$^2$ and 200° to 230° C. respectively. Then, the pressure was released over 1 hour and at the same time the internal temperature was elevated to 250° to 270° C. to heat the contents sufficiently. The autoclave was then cooled and a polyamide was taken out. The polyamide thus obtained showed a relative viscosity, $\eta_{rel}$, of 2.43, a glass transition temperature of 54.3° C. and a melting point of 260° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 17

Example 12 was repeated except that 2-(2'-hydroxyphenyl)benzotriazol-5,5'-dicarboxylic acid was not used to obtain a polyamide. The polyamide thus obtained showed a relative viscosity, $\eta_{rel}$, of 2.35 and a glass transition temperature of 126.7° C.

The ultraviolet absorption behavior of the polyamide is shown in Table 3.

COMPARATIVE EXAMPLE 18

Example 17 was repeated except that 2-(2'-hydroxyphenyl)benzotriazol-5,5'-dicarboxylic acid was not used, to obtain a polyamide. The polyamide thus obtained showed a relative viscosity, $\eta_{rel}$, of 2.22, a glass transition temperature of 86.3° C. and a melting point of 233.2° C.

The ultraviolet absorption behavior of the polyamide is shown in Table 3.

COMPARATIVE EXAMPLE 19

Example 18 was repeated except that 2-(2'-hydroxyphenyl)benzotriazol-5,5'-dicarboxylic acid was not used to obtain a polyamide. The polyamide thus obtained showed a relative viscosity, $\eta_{rel}$, of 2.42, a glass transition temperature of 54.6° C. and a melting point of 262.2° C.

The ultraviolet absorption behavior of the polyamide is shown in Table 3.

COMPARATIVE EXAMPLE 20

Example 12 was repeated except for using 10.6 parts of the 2-(2'-hydroxyphenyl)benzotriazol-5'-carboxylic acid obtained in Comparative Example 1 instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.25 and a glass transition temperature of 126.6° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 21

Example 12 was repeated except for using 106 parts of the 2-(2'-hydroxyphenyl)benzotriazol-5'-carboxylic acid obtained in Comparative Example 1 instead of 10.6 parts of 2-(2'-hydroxyphenyl)benzotriazol-5,5'-dicarboxylic acid to obtain a polyamide. The polyamide thus obtained had a low polymerization degree.

COMPARATIVE EXAMPLE 22

Example 12 was repeated except for using 10.6 parts of the 5-chloro-2-(2'-hydroxyphenyl)benzotriazol-5'-carboxylic acid obtained in Comparative Example 2 instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.21 and a glass transition temperature of 126.3° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 23

Example 12 was repeated except for using 10.6 parts of the 2-(2'-hydroxyphenyl)benzotriazol-3',5'-dicarboxylic acid obtained in Comparative Example 3 instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.28 and a glass transition temperature of 126.4° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 24

Example 12 was repeated except for using 10.6 parts of the 5-chloro-2-(2'-hydroxyphenyl)benzotriazol-3',5'-dicarboxylic acid obtained in Comparative Example 4 instead of 10.6 parts of 2-(2'-hydroxyphenyl)benzotriazol-5,5'-dicarboxylic acid to obtain a polyamide. The polyamide thus obtained showed a relative viscosity, $\eta_{rel}$, of 2.12 and a glass transition temperature of 126.2° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 25

Example 17 was repeated except for using 8.4 parts of the 2-(2'-hydroxyphenyl)benzotriazol-5'-carboxylic acid obtained in Comparative Example 1 instead of 8.4 parts of 2-(2'-hydroxyphenyl)benzotriazol-5,5'-dicarboxylic acid to obtain a polyamide. The polyamide thus obtained showed a relative viscosity, $\eta_{rel}$, of 2.01, a glass transition temperature of 86.5° C. and a melting point of 231.8° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 26

Example 18 was repeated except for using 8.3 parts of the 2-(2'-hydroxyphenyl)benzotriazol-5'-carboxylic acid obtained in Comparative Example 1 instead of 8.3 parts of 2-(2'-hydroxyphenyl)benzotriazol-5,5'-dicarboxylic acid to obtain a polyamide. The polyamide thus obtained showed a relative viscosity, $\eta_{rel}$, of 2.43, a glass transition temperature of 54.3° C. and a melting point of 260.2° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 27

Example 12 was repeated except for using 0.01 part instead of 10.6 parts of 2-(2'-hydroxyphenyl)benzotriazol-5,5'-dicarboxylic acid to obtain a polyamide. The polyamide obtained showed a relative viscosity, $\eta_{rel}$, of 2.33 and a glass transition temperature of 126.3° C.

The polyamide was tested for extractability. Ultraviolet absorption spectra of specimens before and after extraction were compared, and then it was found that both were just the same. The ultraviolet absorption behavior of the specimen after extraction is shown in Table 3.

COMPARATIVE EXAMPLE 28

Example 12 was repeated except for using 10.6 parts of an ultraviolet absorber represented by a structural formula shown below instead of 10.6 parts of 2-(2'-hydroxyphenyl)benzotriazol-5,5'-dicarboxylic acid to obtain a polyamide. The polyamide obtained showed a relative viscosity, $\eta_{rel}$, of 2.20 and a glass transition temperature of 126.4° C.

The polyamide was tested for extractability. The ultraviolet absorption behaviors of the polyamide before and after extraction were compared, and then it was found that both were just the same. The ultraviolet absorption behavior of the specimen after extraction is shown in Table 3.

It is clear from Table 3 that the polyamide has a remarkably lower ultraviolet absorbability than those of Examples 12 through 18.

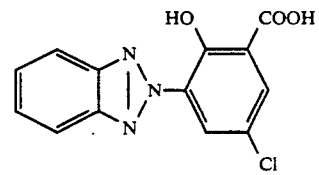

COMPARATIVE EXAMPLE 29

Example 12 was repeated except for using 42.4 parts of an ultraviolet absorber represented by a structural formula shown below instead of 10.6 parts of 2-(2'-hydroxyphenyl)benzotriazol-5,5'-dicarboxylic acid to obtain a polyamide. The polyamide obtained showed a relative viscosity, $\eta_{rel}$, of 1.60 and a glass transition temperature of 115.8° C. Accordingly, the polyamide had a remarkably lower thermal stability than the polyamide obtained in Examples 12 through 16.

The polyamide was tested for extractability. The ultraviolet absorption behaviors of the polyamide before and after extraction were compared, and then it was found that both were just the same. The ultraviolet absorption behavior of the specimen after extraction is shown in Table 3.

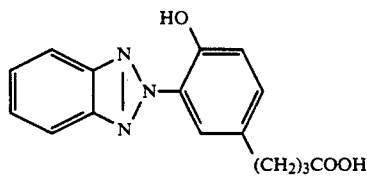

COMPARATIVE EXAMPLE 30

Example 12 was repeated except for using 10.6 parts of an ultraviolet absorber represented by a structural formula shown below instead of 10.6 parts of 2-(2'-hydroxyphenyl)benzotriazol-5,5'-dicarboxylic acid to obtain a polyamide. The polyamide obtained showed a relative viscosity, $\eta_{rel}$, of 2.19 and a glass transition temperature of 126.5° C.

The polyamide was tested for extractability. The ultraviolet absorption behaviors of the polyamide before and after extraction are shown in Table 3.

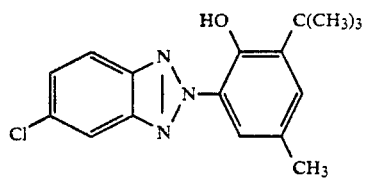
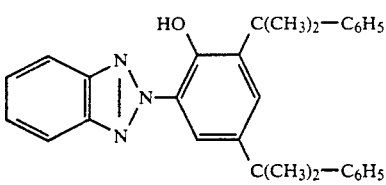

COMPARATIVE EXAMPLE 31

Example 12 was repeated except for using 10.6 parts of an ultraviolet absorber represented by a structural formula shown below instead of 10.6 parts of 2-(2'-hydroxyphenyl)benzotriazol-5,5'-dicarboxylic acid to obtain a polyamide. The polyamide obtained showed a relative viscosity, $\eta_{rel}$, of 2.10 and a glass transition temperature of 126.4° C.

The polyamide was tested for extractability. The ultraviolet absorption behaviors of the polyamide before and after extraction are shown in Table 3.

Obviously, numerous modifications and variations of the present invention are possible in light of the above teachings. It is therefore to be understood that within the scope of the appended claims, the invention may be practiced otherwise than as specifically described herein.

TABLE 3

|  | Relative viscosity $\eta_{rel}$ | Melting point °C. | Glass transition temperature °C. |  | Light transmittance (%) | | | | |
|---|---|---|---|---|---|---|---|---|---|
|  |  |  |  |  | 320 nm | 340 nm | 360 nm | 380 nm | 390 nm | 400 nm |
| Example 12 | 2.26 | — | 126.4 |  | 0 | 0 | 0 | 30.2 | 73.8 | 91.2 |
| Example 13 | 2.10 | — | 127.0 |  | 0 | 0 | 5.1 | 54.7 | 84.1 | 95.6 |
| Example 14 | 2.10 | — | 127.0 |  | 0 | 0 | 0 | 8.1 | 66.4 | 86.7 |
| Example 15 | 2.08 | — | 126.6 |  | 0 | 0 | 0 | 0 | 22.3 | 75.0 |
| Example 16 | 2.08 | — | 126.6 |  | 0 | 0 | 0.5 | 33.1 | 75.3 | 92.8 |
| Example 17 | 2.19 | 230.2 | 86.1 |  | 0 | 0 | 0 | 30.7 | 74.2 | 92.0 |
| Example 18 | 2.43 | 260.0 | 54.3 |  | 0 | 0 | 0 | 30.5 | 74.5 | 91.4 |
| Comparative Example 17 | 2.35 | — | 126.7 |  | 35.5 | 83.5 | 93.3 | 95.5 | 96.0 | 97.6 |
| Comparative Example 18 | 2.22 | 233.2 | 86.3 |  | 91.4 | 95.2 | 96.5 | 98.1 | 98.4 | 98.5 |
| Comparative Example 19 | 2.42 | 262.2 | 54.6 |  | 88.9 | 93.9 | 94.9 | 96.2 | 97.0 | 97.6 |
| Comparative Example 20 | 2.25 | — | 126.6 |  | 0 | 0.7 | 7.5 | 85.8 | 92.7 | 93.8 |
| Comparative Example 21 | — | — | — |  | — | — | — | — | — | — |
| Comparative Example 22 | 2.21 | — | 126.3 |  | 0 | 0.7 | 20.7 | 75.8 | 86.2 | 87.4 |
| Comparative Example 23 | 2.28 | — | 126.4 |  | 0 | 1.0 | 50.0 | 86.4 | 92.3 | 94.2 |
| Comparative Example 24 | 2.12 | — | 126.2 |  | 0 | 1.0 | 42.8 | 75.7 | 92.3 | 97.9 |
| Comparative Example 25 | 2.01 | 231.8 | 86.5 |  | 0 | 0.7 | 7.2 | 84.9 | 93.0 | 94.0 |
| Comparative Example 26 | 2.43 | 260.2 | 54.3 |  | 0 | 0.7 | 7.5 | 85.3 | 93.0 | 94.0 |
| Comparative Example 27 | 2.33 | — | 126.3 |  | 29.8 | 81.2 | 92.0 | 93.8 | 95.8 | 97.4 |
| Comparative Example 28 | 2.20 | — | 126.4 |  | 0 | 0 | 20.8 | 79.6 | 92.2 | 95.0 |
| Comparative Example 29 | 1.60 | — | 115.8 |  | 0 | 0.7 | 8.0 | 86.6 | 93.5 | 98.0 |
| Comparative Example 30 | 2.19 | — | 126.5 | before extraction | 0.5 | 0.5 | 0.5 | 7.3 | 33.5 | 76.6 |
|  |  |  |  | after extraction | 35.3 | 84.2 | 93.3 | 95.3 | 95.9 | 97.5 |
| Comparative Example 31 | 2.10 | — | 126.4 | before extraction | 4.2 | 1.8 | 4.1 | 43.9 | 82.9 | 97.0 |
|  |  |  |  | after extraction | 35.5 | 83.7 | 93.0 | 95.5 | 96.2 | 97.4 |

We claim:

1. A 2-hydroxyphenylbenzotriazol compound represented by the formula (I):

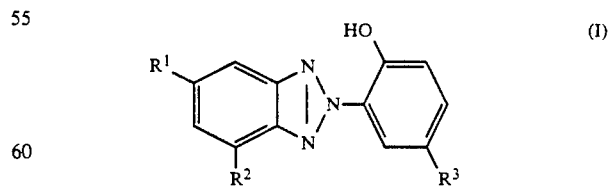

wherein $R^1$ and $R^3$ are each independently a carboxylic acid group, a halogen atom, a lower alkyl group or a lower alkoxyl group; $R^2$ is a carboxylic acid group, a hydrogen atom, a halogen atom, a lower alkyl group or a lower alkoxyl group; and two of $R^1$, $R^2$ and $R^3$ are carboxylic acid groups.

* * * * *